United States Patent
Narayanan Nair et al.

(10) Patent No.: US 10,143,717 B2
(45) Date of Patent: Dec. 4, 2018

(54) POLYHERBAL COMPOSITION FOR IDIOPATHIC PULMONARY FIBROSIS (IPF)

(71) Applicant: AVT Natural Products Ltd, Chennai, Tamil Nadu (IN)

(72) Inventors: Pushpakumari Kaliyarmattom Narayanan Nair, Kerala (IN); Venugopal Kizhikkilot, Tamil Nadu (IN)

(73) Assignee: AVT NATURAL PRODUCTS LTD, Chennai, Tamil Nadu (IN)

( * ) Notice: Subject to any disclaimer, the term of this patent is extended or adjusted under 35 U.S.C. 154(b) by 0 days.

(21) Appl. No.: 15/551,261

(22) PCT Filed: Feb. 8, 2016

(86) PCT No.: PCT/IB2016/050636
§ 371 (c)(1),
(2) Date: Aug. 15, 2017

(87) PCT Pub. No.: WO2016/128875
PCT Pub. Date: Aug. 18, 2016

(65) Prior Publication Data
US 2018/0028592 A1 Feb. 1, 2018

(30) Foreign Application Priority Data
Feb. 15, 2015 (IN) .............. 494/CHE/2015

(51) Int. Cl.
| | | |
|---|---|---|
| *A61K 36/00* | (2006.01) | |
| *A61K 36/9066* | (2006.01) | |
| *A61K 36/82* | (2006.01) | |
| *A61K 36/47* | (2006.01) | |
| *A61K 36/185* | (2006.01) | |
| *A61K 47/38* | (2006.01) | |

(52) U.S. Cl.
CPC ........ *A61K 36/9066* (2013.01); *A61K 36/185* (2013.01); *A61K 36/47* (2013.01); *A61K 36/82* (2013.01); *A61K 47/38* (2013.01)

(58) Field of Classification Search
CPC ..................................................... A61K 36/00
See application file for complete search history.

(56) References Cited

FOREIGN PATENT DOCUMENTS

JP 20060006124 A 7/2007

OTHER PUBLICATIONS

Hamdy, El-Maraghy, and Kortam, Modulatory Effects of Curcumin and Green Tea Extract against Experimentally Induced Pulmonary Fibrosis: A Comparison with N-Acetyl Cysteine, J Biochem Molecular Toxicology,vol. 26, No. 11, 2012, pp. 461-468.
OECD Environmental Health and Safety Publications, Series on Principles of Good Laboratory Practice and Compliance Monitoring (1997), No. 1, pp. 1-41
(ISA/IN) Indian Patent Office, International Search Report for Int'l Appln No. PCT/IB2016/050636, Mar. 21, 2016, 1 pg.

*Primary Examiner* — Qiuwen Mi

(57) ABSTRACT

The present disclosure envisages a polyherbal composition comprising the extracts of *Curcuma longa*, *Camellia sinensis* and *Phyllanthus emblica* for alleviating the symptoms and reduces the clinical progression of Idiopathic pulmonary fibrosis (IPF). Further, the composition comprises at least one pharmaceutically acceptable excipient selected from the group consisting of microcrystalline cellulose, modified starch and maltodextrin. The present disclosure also envisages a process for preparing the poly-herbal composition for alleviating the symptoms of Idiopathic pulmonary fibrosis (IPF).

5 Claims, No Drawings

POLYHERBAL COMPOSITION FOR IDIOPATHIC PULMONARY FIBROSIS (IPF)

FIELD

The present disclosure relates to the field of polyherbal compositions. Particularly, there is envisaged in this disclosure, a polyherbal composition for the treatment of Idiopathic pulmonary fibrosis (IPF).

BACKGROUND

Idiopathic pulmonary fibrosis (IPF) is a chronic progressive lung disorder of unknown etiology in which excessive deposition of collagen-rich extracellular matrix in the alveoli and interstitial tissues of the lung leading to impaired gas exchange and has poor prognosis. IPF is one form of interstitial lung disease (ILD). 'Interstitial' means the disease that affects the 'interstitium', a lace-like network of tissue that supports the alveoli (air sacs) in the lungs. Due to IPF, inflammation or scar, tissue builds up in the lungs, making the lungs thick and hard. Such build-up of the scar tissue makes the lungs stiffer and they lose their elasticity, thus affecting the transport of oxygen. People suffering from IPF feel breathless from simple everyday activities like walking.

IPF represents the end stage of pulmonary inflammation with histopathological characteristics that include an absolute increase of collagen content. It is characterized by disabling dyspnea, extensive interstitial fibrosis and poor gas exchange. Multiple factors, including transforming growth factor (TGF)-$\beta_1$, connective tissue growth factor (CTGF), platelet-derived growth factor (PDGF), inflammatory cytokines, and chemokine (C-C motif) ligand 2/monocyte chemo attractant protein-1 (CCL2) have been implicated in the pathogenesis of IPF.

Although the pathobiology of pulmonary fibrosis has not yet been well clarified, it has generally been hypothesized that activated inflammatory cells which accumulate in the lungs, release harmful amount of reactive oxygen species (ROS) that result in lung injury and proliferation of fibroblast in alveolar walls. IPF is a fatal disorder without any effective therapy till date.

Current treatments for Idiopathic pulmonary fibrosis include corticosteroids and cytotoxic agents such as pirfenidone, cyclophosphamide, azathioprine and colchicines which have significant side effects.

The progressive and fatal course of IPF, coupled with the absence of any effective treatments underscore the need for a solution for this disease which is devoid of any side effects. Accordingly, there is a need to provide a polyherbal composition that is effective and safe for alleviating the symptoms of Idiopathic pulmonary fibrosis, and that has minimum side effects.

OBJECTS

Some of the objects of the present disclosure, which at least one embodiment herein satisfies, are as follows:

It is an object of the present disclosure to provide a polyherbal composition which alleviates the symptoms of Idiopathic Pulmonary Fibrosis (IPF) and also reduces the clinical progression of Idiopathic Pulmonary Fibrosis.

It is another object of the present disclosure to provide a polyherbal composition which is stable.

It is yet another object of the present disclosure to provide a process for producing the polyherbal composition.

It is still another object of the present disclosure to provide a polyherbal composition which can be administered orally.

Other objects and advantages of the present disclosure will be more apparent from the following description, which is not intended to limit the scope of the present disclosure.

SUMMARY

The present disclosure envisages a polyherbal composition, comprising extract of *Curcuma longa*, extract of *Camellia sinensis* and extract of *Phyllanthus emblica*. Further, the composition can also comprise at least one pharmaceutically acceptable excipient selected from the group consisting of, but not limited to, microcrystalline cellulose, modified starch and maltodextrin.

The present disclosure also envisages a process for preparing the polyherbal composition. Typically, the process of the present disclosure involves mixing the extract of *Curcuma longa*, extract of *Camellia sinensis* and extract of *Phyllanthus emblica* in a reaction vessel to form a homogenised mixture. Microcrystalline cellulose, modified starch or maltodextrin are added to the homogenized mixture followed by blending or mixing to obtain the polyherbal composition of the present disclosure.

DETAILED DESCRIPTION

IPF is a chronic and progressive lung disease that results in respiratory failure and death with a median survival rate of about 2 to 4 years from diagnosis. The etiology of IPF remains unknown. As interstitial fibrosis advances with accompanying distortion of lung, the lung becomes less compliant, increasing the effort associated with breathing, leading to dyspnea. Typically, lung function declines slowly over time, but some patients experience rapid decline that can lead to death. Accordingly, there exists a need to develop a solution for alleviating the symptoms of IPF which is devoid of any side effects.

Accordingly, the inventors of the present disclosure, after conducting numerous trials and experiments, have developed a polyherbal composition having a synergistic effect, and mitigating the drawbacks as mentioned above. The polyherbal composition or the present disclosure comprises at least three plant based materials. The polyherbal composition as disclosed in the present disclosure is effective in alleviating the symptoms and reduces the clinical progression of Idiopathic Pulmonary Fibrosis (IPF) without causing any side effects.

In accordance with one aspect of the present disclosure there is provided a polyherbal composition comprising a homogenous blend of:
  i. extract of *Curcuma longa*;
  ii. extract of *Camellia sinensis*; and
  iii. extract of *Phyllanthus emblica*.

*Curcuma longa* is native to the Indian sub-continent, and also grows in Pakistan, Sri-Lanka and Bangladesh.

*Camellia sinensis* is native to East Asia, the Indian Subcontinent and Southeast Asia, and it is known to grow across the world in tropical and subtropical regions.

*Phyllanthus emblica* grows across the world in tropical and subtropical regions, especially India, Nepal, Burma, China (South), Malaysia to Australia (North), Thailand, Indochina and Laos (Khammouan).

The scope of the present disclosure is not only limited to *Curcuma longa*, *Camellia sinensis*, *Phyllanthus emblica* and products derived therefrom but also extends to botanically closely related plants specially belonging to the same family, preferably belonging to the same genus, still preferably belonging to the same species having substantially similar phenotypic and genotypic characteristics.

The plant extracts which can be derived from the bark, roots, tubers, stolons, rhizome, leaves, seeds, fruits, stems and flowers, preferably, rhizomes of *Curcuma longa*, leaves of *Camellia sinensis* and fruit of *Phyllanthus emblica* are commercially purchased from the market as value added products and in an unrecognizable form and extracts were prepared using these value added products.

The extracts may be in the form of a powder obtained by extraction and direct micronization of the plant material or spray drying.

Alternatively, the extracts maybe solid, semi-solid or liquid. Typically, the extracts can be selected from the group that include, but is not limited to, alcoholic, hydro-alcoholic, aqueous, ether, acetone, dichloromethane, chloroform, ethyl acetate, acetone and hexane extract. Typically, the extracts are prepared by using techniques that include, but are not limited to, percolation, decoction, maceration, soxhlet extraction and supercritical fluid extraction.

In an embodiment of the present disclosure, the polyherbal composition comprises a homogenous blend of the extract of *Curcuma longa* in an amount ranging from 10 wt % to 70 wt % to the total weight of the composition, extract of *Camellia sinensis* in an amount ranging from 20 wt % to 40 wt % to the total weight of the composition and extract of *Phyllanthus emblica* in an amount ranging from 1 wt % to 20 wt % to the total weight of the composition.

In another embodiment of the present disclosure, the polyherbal composition comprises a homogenous blend of the extract of *Curcuma longa* in an amount ranging from 30 wt % to 60 wt % of the total weight of the composition, extract of *Camellia sinensis* in an amount ranging from 20 wt % to 40 wt % of the total weight of the composition, extract of *Phyllanthus emblica* in an amount ranging from 5 wt % to 15 wt % to the total weight of the composition and a pharmaceutically acceptable excipient in an amount ranging from 5 wt % to 10 wt % of the total weight of the composition.

Typically, the pharmaceutically acceptable excipient can be selected from the group consisting of, but not limited to, binders, anti-oxidants, pharmaceutically acceptable coating materials.

Typically, the pharmaceutically acceptable excipient is selected from the group consisting of, but not limited to, microcrystalline cellulose, modified starch and maltodextrin.

The polyherbal composition of the present disclosure is non-toxic and has no side effects. Moreover, it also has good stability and is suitable for mass production.

The composition of the present disclosure possesses antibacterial, anti-fungal, anti-inflammatory and anti-microbial properties and helps in alleviating the symptoms and reduces the clinical progression of Idiopathic Pulmonary Fibrosis (IPF).

Typically, the polyherbal composition as disclosed in the present disclosure comprises 30 to 60 wt % of extract of Curcuma longa to the total weight of the composition, 20 to 40 wt % of extract of Camellia sinensis to the total weight of the composition and 5 to 15 wt % of extract of Phyllanthus emblica to the total weight of the composition.

In accordance with another aspect of the present disclosure, there is provided a process for preparing the polyherbal composition.

Typically, the process of the present disclosure involves mixing the extract of *Curcuma longa*, extract of *Camellia sinensis* and extract of *Phyllanthus emblica* in a reaction vessel to form a homogenised mixture. Microcrystalline cellulose, modified starch or maltodextrin is added to the homogenized mixture followed by blending or mixing to obtain the polyherbal composition of the present disclosure.

Typically, the extract of *Curcuma longa* is obtained from the dried rhizomes of turmeric by solvent extraction. The solvents are selected from the group consisting of, but not limited to, acetone, hexane, ethyl acetate, dichloroethane and chloroform. The extraction is carried out at a temperature in the range of 40 to 45° C. to obtain a concentrated product comprising a mixture of turmeric oil and curcuminoids. The analysis of the concentrated product indicated that, the product comprised of 40% curcumin, demethoxy curcumin, bisdemethoxy curcumin and 10% turmeric oil Typically, the extract of *Camellia sinensis* is obtained from the dried leaves of *Camellia sinensis* by solvent extraction followed by purification. The solvents are selected from the group consisting of, but not limited to, a homogenous blend of acetone, water and ethyl acetate. Typically the solvent used is a mixture of acetone and water in the ratio of 20 to 80%. The extraction is carried out at a temperature in the range of 35 to 40° C. to obtain an extracted miscella. This extracted miscella is then desolventised followed by counter extraction by partitioning the extract with ethyl acetate at a temperature in the range of 35 to 40° C. The ethyl acetate portion is then decolorized using activated carbon and decaffeinated using a carbon treatment and then concentrated to form the extracts of *Camellia sinensis*. The analysis of the extract of *Camellia sinensis* indicated that, the extract comprised 95% polyphenol. Out of this 95%, 70% were catechins with EGCG content being 45% and caffeine content being 2%.

Typically, the extract of *Phyllanthus emblica* is obtained from the fresh *Phyllanthus emblica* fruits. These fruits are passed through a juicer to obtain a juice followed by centrifuging to obtain a clarified juice, which is concentrated to 20% solids. This clarified juice is then spray dried in controlled conditions. Analysis of the product showed 45% polyphenols & 2% vitamin C.

In accordance with the embodiments of the present disclosure, the polyherbal composition can be in a dosage form selected from the group consisting of capsules, pills, tablets, mouth dissolving tablet, chewable tablet, effervescent tablet, paste and dried or powdered product for reconstitution with water or other suitable vehicle before use.

The polyherbal composition in an exemplary embodiment of the present disclosure is in the form of capsules.

In one embodiment of the present disclosure, the polyherbal composition is used for alleviating the symptoms of Idiopathic pulmonary fibrosis (IPF).

Typically, there is 15% improvement in the forced vital capacity (FVC) of the patients treated with the polyherbal composition of the present disclosure.

Typically, there is 75% reduction of C reactive protein of the patients treated with the polyherbal composition of the present disclosure.

Typically, there is 48% reduction in the Acute Exacerbation of the patients treated with the polyherbal composition of the present disclosure.

Typically, there is improvement in overall quality of life of the patients treated with the polyherbal composition of the present disclosure.

Typically, there is significantly reduction in the clinical progression of Idiopathic Pulmonary Fibrosis of the patients treated with the polyherbal composition of the present disclosure.

The term "an effective amount" refers to the amount of the polyherbal composition of the present disclosure that is required to confer one of the above-described effects on the subject. The effective amount depends on many factors including the indication of being treated, the route of administration, the overall condition of the patient, weight of the patient, excipient/s used in the composition and the possibility of co-using with other treatment/s. The dose and dose frequency will vary according to the age, body weight, condition and response of the individual consumer or patient.

The present disclosure is further described in light of the following laboratory scale experiments which are set forth for illustration purpose only and not to be construed for limiting the scope of the disclosure. The following experiments can be scaled up to industrial/commercial scale and the results obtained can be extrapolated to industrial/commercial scale.

EXPERIMENT 1

A polyherbal composition in the form of a capsule was prepared by using the following ingredients as given in Table 1. Raw materials of *Curcuma longa*, *Camellia sinensis* and *Phyllanthus emblica* were commercially purchased from the market as value added products and in an unrecognizable form. Then it is made into an extract and formulated to 500 mg capsules.

TABLE 1

| Sr. No. | Ingredients | Quantity (mg) | Quantity (wt %) |
|---|---|---|---|
| 1. | *Curcuma longa* extract | 250 | 50 |
| 2. | *Camellia sinensis* extract | 150 | 30 |
| 3. | *Phyllanthus emblica* extract | 50 | 10 |
| 4. | Microcrystalline cellulose | 50 | 10 |

EXPERIMENT 2

A polyherbal composition in the form of a powder was prepared by using the following ingredients as given in Table 2. Raw materials of *Curcuma longa*, *Camellia sinensis* and *Phyllanthus emblica* were commercially purchased from the market as value added products and in an unrecognizable form. Then it is made into an extract and formulated to 500 mg capsules.

TABLE 2

| Sr. No. | Ingredients | Quantity (mg) | Quantity (wt %) |
|---|---|---|---|
| 1. | *Curcuma longa* Extract | 300 | 60 |
| 2. | *Camellia sinensis* Extract | 150 | 30 |
| 3. | *Phyllanthus emblica* Extract | 50 | 10 |

EXPERIMENT 3: Characterization of the Polyherbal Composition

Testing for Oral Acute Toxicity Study of the Polyherbal Composition in Wistar Albino Rats.

The study was carried out by CARe KERALAM LTD, Kinfra small industries park, Kinfra park P.O., Koratty-680309, Thrissur dist., Kerala. This study was conducted as per the principles of Good Laboratory Practices (GLP) as set forth in the OECD principles of GLP, OECD (ENV/MC/CHEM (98) 17: 1997). The objective of was to assess the toxic potential and to estimate $LD_{50}$ value of the polyherbal composition when administered by oral gavage in a single dose to the Wistar albino rats. Total 5 female rats were used for the study divided into 3 groups:

1. Group I—1 female rat administered with 175 mg/kg of the polyherbal composition.
2. Group II—1 female rat administered with 550 mg/kg of the polyherbal composition.
3. Group III—3 female rats administered with 2000 mg/kg of the polyherbal composition.

The polyherbal composition was administered by oral gavage to each rat daily for 14 days. The dosing of the polyherbal composition was initiated at 175 mg/kg followed by 550 mg/kg and 2000 mg/kg. The mortality, clinical signs, body weight, quantity of food consumed, necropsy and gross pathology in the organs were observed. The treated animals were observed for signs of intoxication at 30 min, 40 min, 1 hour, 2 hour, 3 hour and at 4 hour interval and daily in the morning and again in the afternoon for clinical signs and mortality. The body weights of rats were individually recorded before dosing and at weekly intervals and at terminal sacrifice. At the end of the study haematology parameters were observed. The gross pathological (histopathological) alterations in the organs were observed during necropsy. On $15^{th}$ day, group 1 to 3 was sacrificed by cervical dislocation under euthanasia condition. The organs were collected and used for the histopathological studies.

RESULTS AND DISCUSSION

Mortality: There was no incidence of mortality observed among the female rats exposed to the polyherbal composition at and up to the dose of 2000 mg/kg body wt. The clinical signs, mortality and summary of body weight gain of the rats is summarised in Table 3 and the summary of food and water intake and summary of gross pathological findings is summarised in Table 4.

TABLE 3

| Dose (mg/kg) | No. of animals | Clinical Signs | Mortality | Average Body Weight (g) | | | % Body weight gain | |
|---|---|---|---|---|---|---|---|---|
| | | | | 1-7 days | 8-14 days | 1-14 days | 1-7 days | 1-14 days |
| 175 | 1 | Normal | None | 208 ± 4.5 | 211 ± 3.2 | 211 ± 3.9 | 5 | 7.5 |
| 550 | 1 | Normal | None | 207 ± 3.6 | 211 ± 2.3 | 211 ± 3.0 | 5 | 7.5 |
| 2000 | 3 | Normal | None | 170 ± 7.1 | 186 ± 3.5 | 189 ± 5.3 | 10.7 ± 1.5 | 20.3 ± 1.9 |

TABLE 4

| Dose (mg/kg) | No. of animals | Average Food intake 1-7 days | Average Food intake 8-14 day | Average Food intake 1-14 days | Average Water intake 1-7 days | Average Water intake 8-14 days | Average Water intake 1-14 days | Gross Pathological Findings (Necropsy findings) External | Gross Pathological Findings (Necropsy findings) Internal |
|---|---|---|---|---|---|---|---|---|---|
| 175 | 1 | 16 ± 3.2 | 13.6 ± 2.3 | 12.7 ± 2.7 | 19 ± 1.6 | 20 ± 3.3 | 18 ± 2.4 | No abnormalities detected | No abnormalities detected |
| 550 | 1 | 15 ± 2.7 | 14.3 ± 1.7 | 13.2 ± 2.2 | 21 ± 2.2 | 25 ± 4.4 | 22 ± 3.3 | No abnormalities detected | No abnormalities detected |
| 2000 | 3 | 19 ± 1.8 | 18 ± 1.1 | 19 ± 1.6 | 29 ± 4.8 | 24.6 ± 5.3 | 27 ± 5.1 | No abnormalities detected | No abnormalities detected |

Clinical Signs: Rats treated with the polyherbal composition at and up to the dose of 2000 mg/kg did not induce any remarkable abnormal clinical signs.

Body Weights & Food Consumptions: The polyherbal composition did not induce any remarkable and significant alteration in the body weights of the female rats treated at and up to the dose of 2000 mg/kg of body weight. The rats treated with 2000 mg/kg of the polyherbal composition showed increase in body weight, food and water intake, when compared to Group I and Group II.

Pathology: There were no gross pathological changes or any abnormalities in any of the organs/tissues of the treated rats at and up to the level of 2000 mg/kg detected in any of the sacrificed animals.

DISCUSSION

The polyherbal composition treatment at and up to 2000 mg/kg did not show any mortality and abnormal clinical signs. This observation indicates the absence of toxicity of the polyherbal composition up to the level of 2000 mg/kg in the study. In addition, the diet was well accepted by treated rats suggesting that the polyherbal composition did not possibly cause any alterations in carbohydrate or fat metabolism in experimental animals

CONCLUSION

Results of the study indicated that the polyherbal composition had no adverse effect and did not reveal any clinical signs, mortalities and gross pathological changes due to toxicity on the Wistar rat when treated at and up to the dose level of 2000 mg/kg body weight.

The $LD_{50}$ of test item the polyherbal composition when administered by oral gavage in a single rats was found to be >2000 mg/kg.

EXPERIMENT 4

Evaluation of Efficacy and Safety of the Polyherbal Composition in Patients Suffering from Idiopathic Pulmonary Fibrosis (IPF):

The study was conducted in the Department of Pulmonary Medicine, Sooriya Hospital, Chennai. A total of 50 subjects, 26 males and 24 females, suffering from IPF were enrolled in the study. The age group of the patients was in the range of 45 to 68 years.

Patients were selected with CT scan features of Usual Interstitial Pneumonia variety of Idiopathic Pulmonary Fibrosis, High-resolution computed tomography (HRCT) evidence of definite or probable Usual interstitial pneumonia (UIP) pattern, in the appropriate clinical settings were required before including into the study. Definite UIP pattern was defined by basal predominant, sub pleural reticular abnormality with traction Bronchiectasis and honey comb cysts. Patients had other clinical features of clubbing, Bibasilar crackles and abnormal PFTs and DLco.

Patients unwilling for conventional therapy or those who could not tolerate the conventional therapy were included in the polyherbal composition group. These patients were not allowed to use steroids or immuno suppressive therapy and were administered with the polyherbal composition. The dosage was 500 mgs of the polyherbal composition three times daily. The non polyherbal composition group received steroids and immuno suppressive therapy.

Initially, upon evaluation, the basic Arterial Blood Gas (ABG) values showed the partial pressure of oxygen in the blood, i.e. PaO2>80 mm Hg and Sp02 was 88% or less during exertion. The Spirometry base line was:

Forced vital capacity (FVC): 1.42 Lts (Pred 2.30 Lts.)

Forced expiratory volume 1 (FEV1): 0.98 Lts (Pred 1.68 Lts.)

The patients were observed for a period of two years with once a month follow up. The polyherbal composition group received supportive drugs other than Steroids/Azathioprim/N Acetyl Cystine, whereas the non polyherbal composition group received Steroids/NAC and Azathioprim.

Out of the 50 people initially enrolled, 4 patients died during the study period and the rest 46 were available for analysis.

Upon analysis, no significant change was observed radiologically in both the groups at the end of the study. Significant improvement was noted from the Base line FVC to the end of the study FVC in the polyherbal composition group which was around 15% (P 0.001), which is summarized in Table 5.

TABLE 5

| | FVC Base line | FVC Post study | % change |
|---|---|---|---|
| Polyherbal composition group | 1.32 Lts. | 1.52 Lts. | 15% |
| Non polyherbal composition group | 1.48 Lts. | 1.30 Lts | −15% |

Upon analysis, the ABG values—(Pao2) showed 5% improvement in the polyherbal composition group, whereas the non polyherbal composition group patients showed −8% reduction in PaO2 (Partial pressure of oxygen)values, as summarized in Table 6.

TABLE 6

|  | PaO2 Baseline | Post study | 0% |
|---|---|---|---|
| Polyherbal composition group | 82% | 86% | 5% |
| Non polyherbal composition group | 84% | 76% | −8% |

Significant reduction of about 75% was observed in C Reactive protein values in the polyherbal composition group which is summarized in Table 7.

TABLE 7

|  | Before (CRP Units) | After (CRP Units) |
|---|---|---|
| Polyherbal composition group | 68 | 17 |
| Non polyherbal composition group | 56 | 54 |

The number of incidents of acute exacerbations was reduced to 48% in the polyherbal composition group as compared to the non polyherbal composition group. Acute exacerbations were significant in the non polyherbal composition group and they required Hospitalization for supportive care. They also needed heavy dose of antibiotics and corticosteroids, along with oxygen supplementation. Overall quality of life was better in the polyherbal composition group. (P=0.0001). However DLco values in both groups did not show any change.

The polyherbal composition group patients showed reduction in acute exacerbations in the 6 minute walk distance. No adverse events were reported from the polyherbal composition group. The dose of 500 mgs three times daily was well tolerated by the patients during the two years study period. Periodic liver function and renal function test were normal in the study group.

Conclusion: The polyherbal composition group showed encouraging evidence for the routine use in IPF patients. Significant reduction in acute exacerbations and hospitalizations were observed in the polyherbal composition group and the quality of life was also better in this group. Changes in FVC and 6-min walk test results were strikingly significant.

EXPERIMENT 5

Stability study of the polyherbal composition was carried out according to the International Conference on Harmonisation (ICH) guidelines. The results obtained are summarised in Table 8. The study was carried out at 30° C. at 65% humidity for 24 months. The polyherbal composition showed good stability over the study period of 24 months.

TABLE 8

| Parameters | Month : 0 | Month: 3 | Month: 6 | Month: 9 | Month: 12 | Month: 18 | Month: 24 |
|---|---|---|---|---|---|---|---|
| Color & Appearance | Yellowish Powder | Yellowish Powder | Yellowish Powder | Yellowish Powder | Yellowish Powder | Yellowish Powder | Yellowish Powder |
| Total Polyphenols | 36.0 | 36.0 | 35.9 | 35.9 | 35.7 | 35.6 | 35.6 |
| Total Catechins | 21.8 | 21.8 | 21.8 | 21.6 | 21.6 | 21.6 | 21.5 |
| EGCG (Epigallocatechin gallate) | 13.6 | 13.6 | 13.6 | 13.5 | 13.5 | 13.4 | 13.4 |
| Curcuminoids | 25 | 25 | 24.8 | 24.8 | 24.8 | 24.7 | 24.7 |
| Turmeric Oil | 7 | 7 | 7 | 6.8 | 6.8 | 6.7 | 6.7 |
| Vitamin C | 0.3 | 0.3 | 0.3 | 0.28 | 0.28 | 0.26 | 0.26 |
| Total plate count (Cfu = colony-forming unit) | 10 Cfu/G | 10 Cfu/G | 10 Cfu/G | 30 Cfu/G | 30 Cfu/G | 30 Cfu/G | 30 Cgu/G |
| Yeast and Mould | Not detected | Not detected | Not detected | Not detected | Not detected | Not detected | Not detected |
| E-coli | Negative | Negative | Negative | Negative | Negative | Negative | Negative |
| Salmonella | Negative | Negative | Negative | Negative | Negative | Negative | Negative |

TECHNICAL ADVANCEMENTS

The present disclosure described herein above has several technical advantages including, but not limited to, the realization of:
- a polyherbal composition which has a quick onset of action;
- a polyherbal composition for alleviating the symptoms of common cold, sore throat, cough and bronchitis;
- a polyherbal composition which can also be used as a rejuvenator and as an immunomodulator; and
- a process for producing a polyherbal composition which is devoid of any side effects and is nontoxic.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A polyherbal composition comprising:
   i. extract of *Curcuma longa* in an amount ranging from 10 wt % to 70 wt % of the total weight of the composition;
   ii. extract of *Camellia sinensis* in an amount ranging from 20 wt % to 40 wt % of the total weight of the composition; and
   iii. extract of *Phyllanthus emblica* in an amount ranging from 1 wt % to 20 wt % of the total weight of the composition;
   wherein the polyherbal composition synergistically alleviates the symptoms of Idiopathic pulmonary fibrosis (IPF).

2. The polyherbal composition of claim 1, further comprises at least one pharmaceutically acceptable excipient selected from the group consisting of microcrystalline cellulose, modified starch and maltodextrin in an amount ranging from 5 wt % to 10 wt % of the total weight of the composition.

3. The polyherbal composition of claim 1, wherein the extract of *Curcuma longa* in an amount ranging from 30 wt % to 60 wt % of the total weight of the composition.

4. The polyherbal composition of claim 1, wherein the extract of *Phyllanthus emblica* comprises an amount ranging from 5 wt % to 15 wt % of the total weight of the composition.

5. The polyherbal composition of claim 1, where in the extract of *Camellia sinensis* is in an amount ranging from 25 wt % to 35 wt % of the total weight of the composition.

* * * * *